United States Patent [19]

Carter et al.

[11] 4,294,247

[45] Oct. 13, 1981

[54] FRANGIBLE, RESEALABLE CLOSURE FOR A FLEXIBLE TUBE

[75] Inventors: Garry L. Carter, Palatine; Daniel B. Granzow, Arlington Heights; Edward L. Bayham, Mundelein, all of Ill.

[73] Assignee: Baxter Travenol Laboratories, Inc., Deerfield, Ill.

[21] Appl. No.: 15,395

[22] Filed: Feb. 26, 1979

Related U.S. Application Data

[63] Continuation of Ser. No. 818,357, Jul. 25, 1977, abandoned.

[51] Int. Cl.$^3$ ............................................. A61M 5/00
[52] U.S. Cl. ......................... 128/214 D; 128/272.3; 137/68 R; 150/8
[58] Field of Search ............ 137/68 R, 797; 251/342; 128/214 R, 214.2, 214 D, 247, 272, 272.3; 150/8

[56] References Cited

U.S. PATENT DOCUMENTS

| | | | |
|---|---|---|---|
| 1,913,116 | 6/1933 | Haimbaugh | 137/533.17 |
| 3,158,165 | 11/1964 | Benson et al. | 137/68 R |
| 3,470,893 | 10/1969 | Nelson | 137/68 R |
| 3,482,572 | 12/1969 | Grosclaude et al. | 128/214 D |
| 3,509,879 | 5/1970 | Bathish et al. | 128/272 X |
| 3,685,795 | 8/1972 | Caster | 251/342 |
| 4,007,738 | 2/1977 | Yoshino | 128/214 D |
| 4,055,179 | 10/1977 | Manschot et al. | 128/274 X |
| 4,080,965 | 3/1978 | Phillips | 251/342 X |

FOREIGN PATENT DOCUMENTS

| | | | |
|---|---|---|---|
| 49-10156 | 11/1974 | Japan | 137/68 R |
| 402286 | 5/1966 | Switzerland | 128/214 D |
| 497181 | 11/1970 | Switzerland | 137/68 R |

*Primary Examiner*—Robert G. Nilson
*Attorney, Agent, or Firm*—Paul Flattery; Daniel Ryan; Garrettson Ellis

[57] ABSTRACT

In a flexible tube, for example tubing for connecting blood bags, valve means are provided which comprises a tubular portion having a closed end, and an elongated, generally rigid member carried on the exterior of the closed end and positioned within the flexible tube. Frangible means are provided to permit the opening of the closed end by manual manipulation of the elongated member from outside of the flexible tube. The elongated, rigid member is adapted to fit in sealing relationship within the tubular portion after the opening of the closed end, to permit resealing of the valve.

11 Claims, 6 Drawing Figures

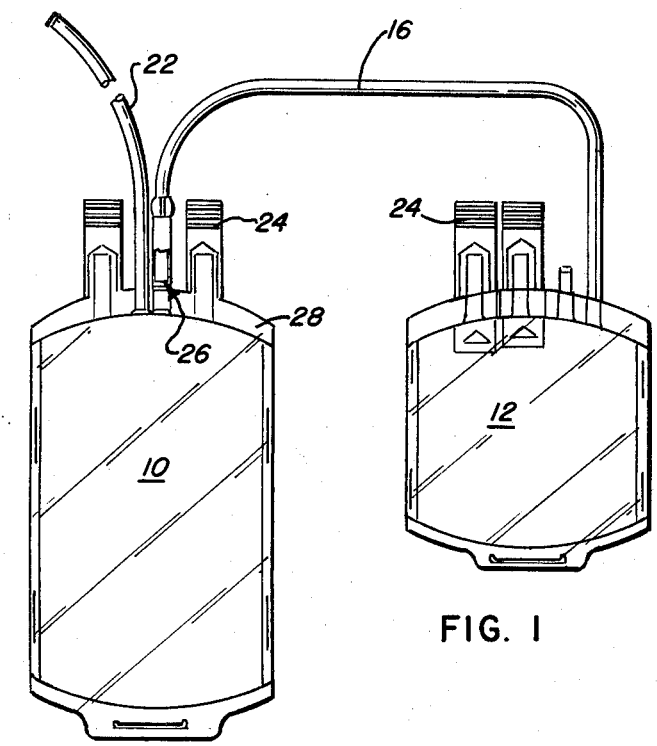
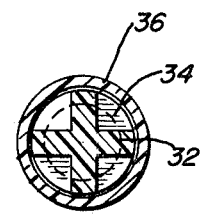
FIG. 1
FIG. 6
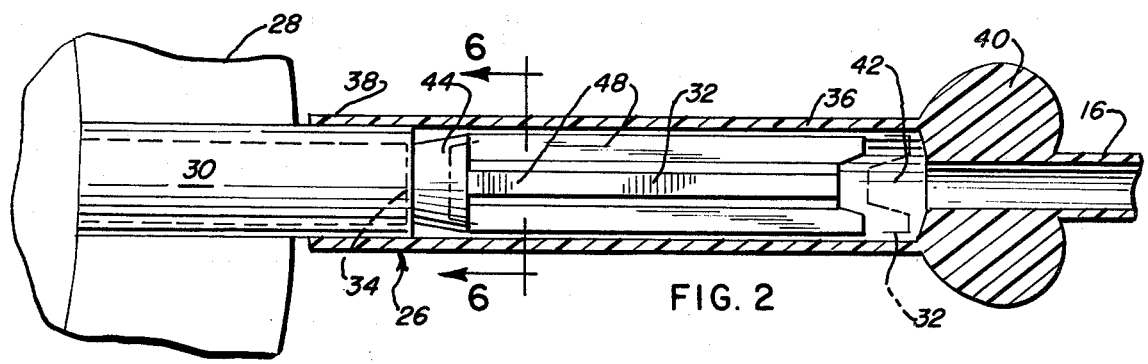
FIG. 2
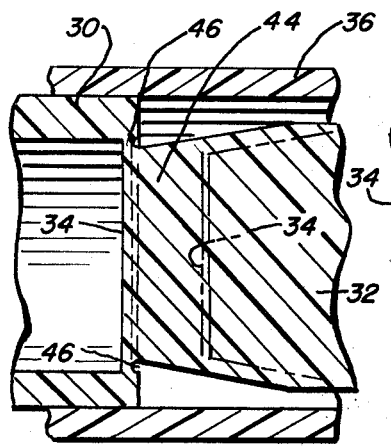
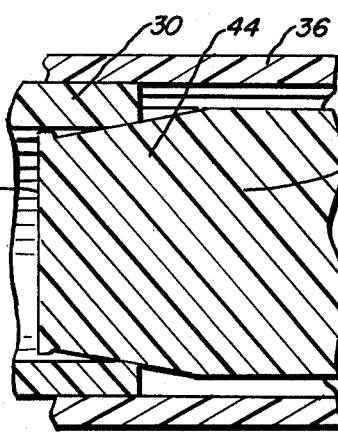
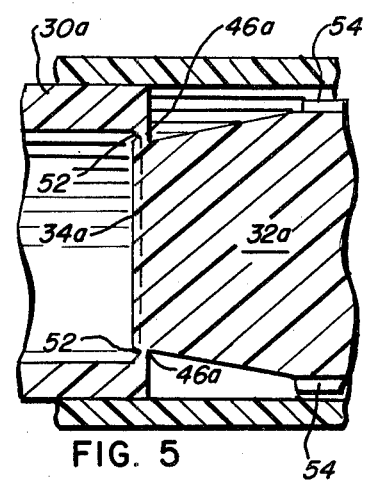
FIG. 3    FIG. 4    FIG. 5

FRANGIBLE, RESEALABLE CLOSURE FOR A FLEXIBLE TUBE

This application is a continuation of U.S. application Ser. No. 818,357, filed July 25, 1977 and since abandoned.

BACKGROUND OF THE INVENTION

In multiple blood bags and the like, it is desirable to provide an initial seal in the tubing between the multiple blood bags which can be opened without breaking the sterility within the system. This has been done in the past by various types of pointed cannulas positioned within the tubing itself and manipulated from the outside, to penetrate a diaphragm or membrane closing off the tubing. Also, a ball may be wedged into the tubing between the blood bags, to be removed by squeezing it out of the tubing to drop into the bag for opening of the valve.

Other breakaway structures within the tubing are known, so that, by manipulation from outside of the tubing, a rigid, closed-end tubular structure is broken in the middle to open a flow channel through the tubing. These structures, however, exhibit the disadvantage that they cannot be resealed once they have been opened. Also, they exhibit some difficulty of manipulation and use.

DESCRIPTION OF THE INVENTON

In accordance with this invention, a valve-type seal for a flexible tube is provided for connection tubing between blood bags, or any other desired use where valving of fluid flow is desired in a flexible tube without direct access to the interior of the tube. The valve of this invention is also resealable, which permits the closing once again of flow through the tube, and reopening again when and as desired.

In this invention, valve means are provided for a flexible tube which comprises a tubular portion having a closed end. An elongated, generally rigid member is carried on the exterior of the closed end and positioned within the tube. Frangible mens, for example, at least one annular line of tearing weakness positioned at the closed end of the tubular portion, are provided, to permit the opening of the closed end by manual manipulation of the elongated member from outside of the frangible tube by bending the elongated member. Also, the elongated member is adapted to fit in sealing relation within the tubular portion after opening of the valve, to permit resealing thereof.

The elongated member may carry vanes along its length to provide fluid flow channels along it, so that the member does not obstruct flow within the tube.

In the drawings,

FIG. 1 is a plan view of a multiple blood bag utilizing this invention.

FIG. 2 is a greatly enlarged view of the valve of this invention as shown in FIG. 1, with some of the parts shown in longitudinal section.

FIG. 3 is a further enlarged view of a portion of FIG. 2, taken partly in section, showing the closed end of the tubular portion of a porton of the elongated member in its original condition.

FIG. 4 is a view similar to FIG. 3, showing the same structure after the valve of this invention has been opened and then resealed.

FIG. 5 is a greatly enlarged view similar to FIG. 3, but showing a modification of the structure.

FIG. 6 is a sectional view taken along line 6—6 of FIG. 1.

Referring to the drawings, the invention of this application is shown in a double bag system which comprises blood bags 10, 12 connected together by length of tubing 16 in a known manner. It is of course contemplated that the invention of this application may be used well with triple and quadruple bag systems, as desired, or any other system for use in the medical field or elsewhere where valving inside of a flexible tube, controllable from the outside, is desired.

Blood bag 10 carries conventional donor tubing 22, only a fragment of which is shown, plus access ports 24 similar to those which are at the present time commercially available.

In accordance with this invention, valve means 26 is provided in the blood bag system, being sealingly retained in flow communication with blood bag 10, passing through the heat-sealed walls 28 of the blood bag as particularly shown in FIG. 2.

As previously described, the valve means 26 comprises a tubular portion 30, which is shown to be the portion retained by and passing through heat sealed portion 28 of the blood bag. Preferably, tubular portion 30 is formed to be of rigid plastic, and is molded integrally with elongated, generally rigid member 32, to form a single piece.

Tubular portion 30 defines a closed end 34. Elongated, rigid member 32 is carried on the exterior of the closed end as shown in FIG. 2, and is positioned within flexible tube 36 in sealed manner.

Flexible tube 36 may be sealed at one end 38 to tubular portion 30 by conventional solvent or heat sealing, and is crimped in the conventional manner at its other end 40 for sealing connection to tubing 16, which may be of narrower diameter. Accordingly, flexible tube 36, as part of tubing 16, which may be also flexible, provides an enlarged chamber in the flow line to receive elongated, generally rigid member 32.

It will be noted that the enlarged chamber defined by tubing 36 may be fashioned to be somewhat longer than elongated member 32 to provide a space 42 for elongated member 32 to withdraw from its integral connection with tubular member 30.

Elongated member 32 defines a forwardly positioned, tapered portion 44 connected to closed end 34 of tubular member 30.

Frangible means, specifically embodied in FIG. 3 by an annular line of tearing weakness 46, extending completely around the front end of tapered portion 44 and defined in closed end 34, is provided. This line of tearing weakness is formed by a zone of decreased thickness at line of tearing weakness 46, defined between tapered portion 44 and tubular portion 30. Accordingly, when one wishes to open valve 26, one simply grasps tubing 36 with the fingers and bends or twists rigid, elongated member 32 until a fracture takes place about annular line of weakness 46. Then, elongated member 32 can be moved rearwardly in the manner shown in FIG. 2 by the phantom lines, to remove end 34 of tubing 30 out of the way, and to open a flow channel through the valve.

In accordance with this invention, tapered portion 44 of the elongated member 32 is proportioned so that, when one desires to reseal the valve of this invention, one can press tapered portion 44 through the open end of tubular member 30 to form a tight, obstructing seal of fluid flow through tubublar member 30, as shown in FIG. 4. Accordingly, in this configuration, the structure that was initially end 34 of tube 30, is pressed inwardly from the end of the tube 30 as shown.

Thereafter, as desired, one can manually manipulate elongated member 32 into or out of sealing relationship with tubular member 30, to open and close the valve as one may desire.

Elongated member 32 defines a series of radial vanes 48, to be of a cross-shaped cross secton, to provide longitudinal flow channels between the vanes for facilitating flow. Also, the diameter of outer tube 36 is proportioned to be larger than the largest transverse dimension of elongated member 32 so that, when broken off from tubular member 30, fluid can easily flow around member 32 except when the member is put into position as shown in FIG. 4 to block flow through tubular member 30.

Referring to FIG. 5, a slightly modified embodiment of the apparatus described above is shown. In this embodiment, which is otherwise identical to the embodiment described above, annular groove 52 is provided in end wall 34a of tubular member 30a. Accordingly, upon manipulation of elongated, generally rigid member 32a in a manner similar to that of the previous embodiment, tearing takes place in an annular region in the vicinity of groove 52 and weakened area 46a with somewhat greater ease than in the previous embodiment, because of groove 52. This embodiment can be used; when desired, with particularly tough plastic materials or in the instance that the dimensions of the device are large.

Also, stop members 54 may be provided, to prevent excessive penetration of rigid member 32a into tubular member 30a.

The structure of this invention is easy to mold, and performs reliably on a mass-produced basis.

The above has been offered for illustrative purposes only, and is not for the purpose of limiting the invention of this application, which is as defined in the claims below.

That which is claimed is:

1. In a flexible tube, valve means which comprises: a tubular portion having a closed end; an elongated, generally rigid member carried on the exterior of said closed end and positioned within said flexible tube; and frangible means to permit the opening of said closed end by manual manipulation of said elongated member from outside of the flexible tube, to separate said elongated member from the tubular portion and to open said closed end, said elongated rigid member being adapted to fit in sealing relation within said tubular portion after said opening to permit resealing of the valve.

2. The valve means of claim 1 in which the end of said generally rigid member which is adjacent said frangible means is tapered to facilitate said fitting in sealing relation within the tubular portion.

3. The valve means of claim 1 in which said frangible means comprises an annular line of tearing weakness positioned at said closed end of the tubular portion.

4. The valve means of claim 1 in which said elongated, generally rigid member defines longitudinal vanes to provide flow channels along its length.

5. The valve means of claim 4 which is part of a multiple blood bag system.

6. The valve means of claim 5 in which said tubular member is carried within a sealed edge of a blood bag with the closed end of said tubular member pointed outwardly.

7. The valve means of claim 6 in which said annular line of bearing weakness includes an annular groove defined in said closed end on the side thereof opposite from the elongated, generally rigid member.

8. A flexible collapsible container comprising
a sealed edge peripherally defining an interior,
a flexible tube communicating with said interior and the atmosphere,
a tubular valve member carried within said sealed edge of said container and extending into said flexible tube, said tubular valve member including a closed end wall blocking flow communication through said flexible tube,
an elongated, generally rigid member carried on the exterior of said closed end wall and extending within said flexible tube outwardly from said end wall away from said container interior, and
frangible annuular groove means on said closed end wall and defining thereon an annular zone of weakness operative for opening said closed end wall by breaking about said annular zone in response to manual manipulation of said elongated member from outside of said flexible tube to thereby open flow communication through said flexible tube.

9. A flexible collapsible container according to claim 8 wherein said elongated, generally rigid member defines longitudinal vanes to provide flow channels along its length.

10. A flexible collapsible container according to claim 9 which is part of a multiple blood bag system.

11. In a flexible tube, valve means which comprises: a tubular portion having a closed end; an elongated, generally rigid member carried on the exterior of said closed end and positioned within said flexible tube; frangible means to permit the opening of said closed end by the breaking of said closed end about an annular zone of weakness by manual manipulation of said elongated member from outside of the flexible tube, for opening of said valve, said elongated, generally rigid member defining longitudinal vanes to provide flow channels along its length.

* * * * *